(12) United States Patent
Jansen et al.

(10) Patent No.: US 8,114,864 B2
(45) Date of Patent: Feb. 14, 2012

(54) MACROLIDE ANTIBIOTICS AND THEIR USE FOR MEDICAL PURPOSES

(75) Inventors: Rolf Jansen, Braunschweig (DE); Brigitte Kunze, Braunschweig (DE); Herbert Irschik, Wolfenbuttel (DE)

(73) Assignee: Helmholtz-Zentrum Fuer Infektionsforschung, Braunschweig (DE)

( * ) Notice: Subject to any disclaimer, the term of this patent is extended or adjusted under 35 U.S.C. 154(b) by 193 days.

(21) Appl. No.: 12/515,695

(22) PCT Filed: Nov. 9, 2007

(86) PCT No.: PCT/EP2007/062107
§ 371 (c)(1),
(2), (4) Date: May 20, 2009

(87) PCT Pub. No.: WO2008/068127
PCT Pub. Date: Jun. 12, 2008

(65) Prior Publication Data
US 2010/0113757 A1    May 6, 2010

(30) Foreign Application Priority Data
Dec. 4, 2006 (EP) .................................. 06125361

(51) Int. Cl.
*A61K 31/395* (2006.01)
*C07D 487/04* (2006.01)

(52) U.S. Cl. ........................................ 514/183; 540/468
(58) Field of Classification Search ................ 540/468; 514/183; 548/152, 146
See application file for complete search history.

(56) References Cited

FOREIGN PATENT DOCUMENTS
WO    WO 97/18217    5/1997

OTHER PUBLICATIONS

Grant & Hackh'S Chemical Dictionary (5th Ed. 1987), p. 148.*
Heinrich Steinmetz et al., "Thuggacins, Macrolide Antibiotics Active Against *Mycobacterium Tuberculosis* Isolation from Myxobacteria, Structure Elucidation, Conformation Analysis and Biosynthesis", *Chemistry: A European Journal*, vol. 13, 2007, pp. 5822-5832.

* cited by examiner

*Primary Examiner* — Jason M Nolan
(74) *Attorney, Agent, or Firm* — Greer, Burns & Crain Ltd.

(57) ABSTRACT

The invention provides novel Thuggacin-Type macrolide compounds which form rearrangement products forming a lacton bond to different carbon atoms. The novel compounds can be produced by fermentation of *Sorangium cellulosum* and *Chondromyces crocatus* and can be isolated by adsorption and chromoatograhic processing steps. The compounds are found to have antibiotic activity. The invention also relates to Thuggacin A, Thuggacin B, Thuggacin C, 13-Methyl-Thuggacin A, Thuggacin CMC-A, Thuggacin CMC-B and Thuggacin CMC-C AS Antimycobacterial Agents.

14 Claims, 1 Drawing Sheet

MACROLIDE ANTIBIOTICS AND THEIR USE FOR MEDICAL PURPOSES

Figure 1:
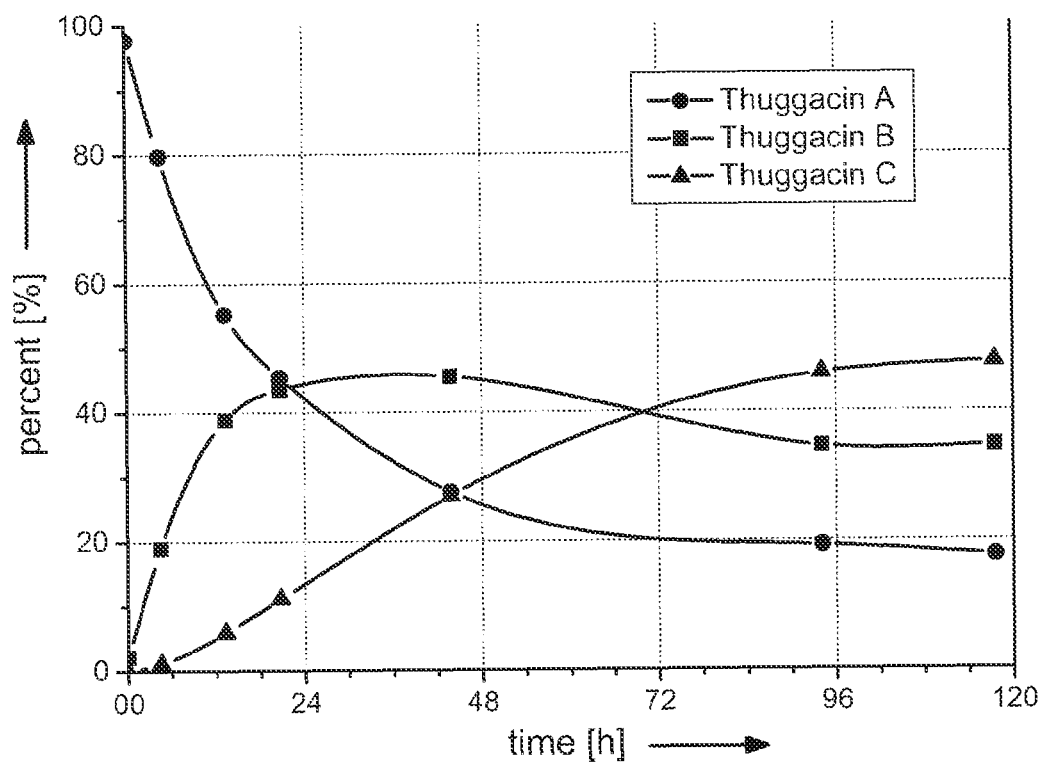

The present invention relates to the novel use of thuggacins, which can be classified as macrocyclic lactones and macrolide antibiotics, respectively.

In general, the present invention relates to the use of thuggacin A and thuggacin B for the production of a pharmaceutical composition effective against mycobacteria, e.g. *Mycobacterium tuberculosis, M leprae*, and *M. chitae* as well as against *Corynebacterium* spp.

In a further aspect, the present invention relates to novel compounds belonging to the class of thuggacins, namely thuggacin C, 13-methyl thuggacin A, thuggacin cmc-A, thuggacin cmc-B and thuggacin cmc-C, as well as their use for medical purposes, namely their use as antibiotics against inter alia the above-mentioned pathogens.

Further, the present invention relates to a composition comprising at least one of thuggacin A, 13-methyl thuggacin A, thuggacin B, and/or thuggacin C, which composition is stabilized against alterations in the composition and/or concentration of thuggacin A, -B and/or -C, respectively.

In addition, the present invention relates to a composition comprising at least one of thuggacin cmc-A, thuggacin cmc-B and thuggacin cmc-C, which composition is preferably stabilized against alterations in the composition and/or concentration of its components.

STATE OF THE ART

WO 97/18217 discloses thuggacin A having the structure I:

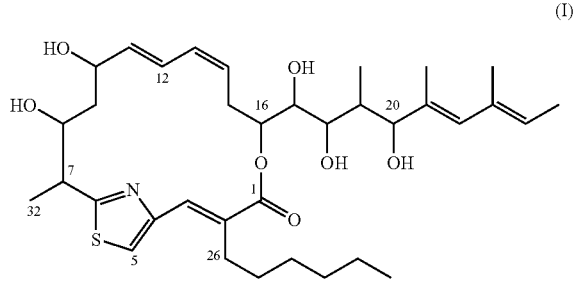

and thuggacin B, having the structure II:

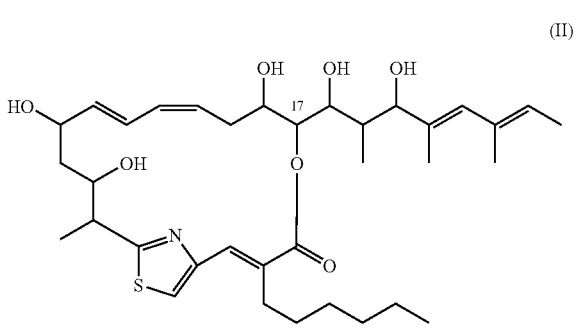

Further, WO 97/18217 generally discloses that thuggacin A and thuggacin B can be isolated from a culture of *Sorangium cellulosum* and have been found to have bactericidal activity against selected species and/or antimycotic activity.

Myxobacteria are generally described in Reichenbach, H. and Dworkin, M. (1992), The myxobacteria. In *The Prokaryotes*, 2$^{nd}$ edn, pp. 3416-3487. Edited by A. Balows, H. G: Trüper, M. Dworkin, W. Harder & K. H. Schleifer. New York: Springer, and Reichenbach, H. (2005) Order VIII. *Myxococcales* Tchan, Pochon and Prévot 1948, 398$^{AL}$ in Bergey's Manual of Systematic Bacteriology, 2$^{nd}$ edition, vol. 2, part C, pp. 1059-1072. Edited by D. J. Brenner, N. R. Krieg, J. T. Staley & G. M: Garrity. New York: Springer.

OBJECTS OF THE INVENTION

In view of the known compounds described as thuggacin A and thuggacin B, the present invention seeks to provide a novel use for medical application of the known compounds, as well as novel compounds belonging to the class of thuggacins, methods for their production, and the use of the novel compounds for the production of pharmaceutical compositions for medical use based on the antimicrobial activity of the compounds.

Further, it has been discovered during the development leading to the present invention that thuggacin A and thuggacin B are not stable in aqueous solution, optionally comprising a $C_1$-$C_2$ alcohol. Accordingly, it is a further objective of the present invention to provide a composition providing stability to thuggacin A, thuggacin B and, preferably, to the novel compounds.

GENERAL DESCRIPTION OF THE INVENTION

The present invention attains the above-mentioned objects by providing the use of known thuggacin A and thuggacin B for use in the production of pharmaceutical compositions effective against mycobacteria and further pathogenic microorganisms, e.g. against *Corynebacterium* spp., and by providing a novel compound presently termed thuggacin C as well as novel compounds termed thuggacin cmc-A, thuggacin cmc-B and thuggacin cmc-C.

Further, when investigating thuggacin A and thuggacin B, it was found that the known compounds are present in an equilibrium with each other and with thuggacin C, when in a protic solvent, e.g. in aqueous solution, especially in aqueous solution comprising an alcohol, e.g. methanol, or a solvent like acetone or DMSO. Similarly, an equilibrium was observed between the novel thuggacin cmc-A, thuggacin cmc-B and thuggacin cmc-C.

For providing stability to compositions comprising a thuggacin of the invention in a protic solvent, e.g. provided in an aqueous composition, the invention provides that the thuggacin composition is adjusted to a pH value at which rearrangement reactions are essentially suppressed. The stabilisation of the thuggacin composition according to the invention is also used in an embodiment of a solid composition for medical use because the application of the composition to a patient comprises contacting of the composition with protic compositions, e.g. with body fluid, which contacting would allow the rearrangement reactions to occur.

It was found that the addition of an acid, preferably an organic acid, even in trace amounts, leads to a stabilisation of the relative proportions of thuggacin A, 13-methyl thuggacin A, thuggacin B and thuggacin C in the aqueous composition. This stabilisation is also applicable to thuggacin cmc-A, thuggacin cmc-B and thuggacin cmc-C, respectively. In general, stabilisation of thuggacins is caused by a pH value in the pH range of about 3.5 to 9, preferably 3.5 to 7. In addition to or in alternative to adjusting the pH of a thuggacin comprising composition by adding acid or base, buffer substances can be used, e.g. pharmaceutically acceptable buffers.

Analysis of the biological activity of thuggacin A, 13-methyl thuggacin A, thuggacin B and thuggacin C demonstrated their antibiotic activity against clinical isolates as well as against reference strains of *Mycobacterium tuberculosis*. Initial studies indicate that thuggacin A, 13-methyl thuggacin A, thuggacin B and thuggacin C are active against mycobacteria and *corynebacteria*. When investigating the effect, the aforementioned thuggacins were found to cause an inhibition of the electron transport chain, impairing bacterial cell respiration, e.g. inhibiting the oxygen demand of *Micrococcus luteus* at concentrations of about 2 ng/mL in liquid culture and essentially inhibiting NADH oxidation of crude cytoplasmic membrane fractions at about 10 ng/mL.

Accordingly, the present invention provides the use of thuggacin A, 13-methyl thuggacin A, thuggacin B and/or thuggacin C, alone or in combination with one another for the preparation of a pharmaceutical composition active against mycobacteria, comprising e.g. *Mycobacterium tuberculosis, Mycobacterium leprae, Mycobacterium phlei* and *Mycobacterium chitae*, as well as against *corynebacteria*. In a preferred embodiment, the pharmaceutical composition is stabilized by a content of the least one acid, preferably of an organic acid, which can be selected from the group comprising e.g. acetic acid, lactic acid, propionic acid, succinic acid and/or phosphate buffer.

Preferably, the pharmaceutical composition has a pH in the range of 5.5 to 8.

Further, the present invention provides 13-methyl thuggacin A and thuggacin C as novel compounds useful for the production of pharmaceutical compositions, e.g. effective against bacteria, especially against mycobacteria.

The novel compounds 13-methyl thuggacin A and thuggacin C can be isolated from fermentation broth of *Sorangium cellulosum*, e.g. using strain So ce 895.

The chemical structure of thuggacin C could be determined to III:

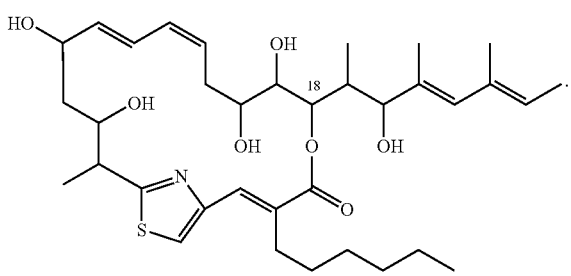

(III)

From the equilibrium reactions of thuggacin A, thuggacin B and thuggacin C in protic solvent, e.g. in aqueous solution, preferably comprising an alcohol, it was found that thuggacin C is a structural isomer of thuggacin A and/or of thuggacin B, obtainable by rearrangement of the lactone bond, e.g. as a transesterification reaction product.

When screening another member of myxobacteria, namely chondromyces strains, further compounds could be identified, which can be regarded as formal structural isomers and/or substitution variants of thuggacin C. In detail, a compound having the following structure IV, presently termed thuggacin cmc-A was identified, which can be regarded formally as a transesterification product of thuggacin C, carrying an additional hydroxyl group at C-32 and lacking both the n-pentyl group substituting C-26 and the hydroxyl group substituting C-20 in thuggacin C. Accordingly, thuggacin cmc-A can also be regarded as a structural variant of thuggacin A.

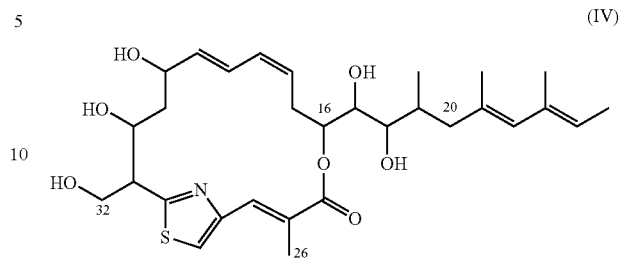

(IV)

Further, a compound having a structure according to formula VI, presently termed thuggacin cmc-C could be identified, that can also be formally regarded as a substitution variant of thuggacin C, having an additional hydroxyl group substituting C-32 and lacking both the n-pentyl group substituting C-26 and the hydroxyl group substituting C-20 in thuggacin C.

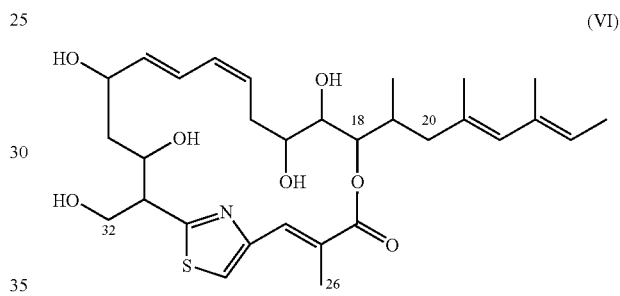

(VI)

As described for the rearrangement of the lacton bond between thuggacin A, thuggacin B and thuggacin C, a rearrangement product of thuggacins cmc-A and cmc-C was found and named thuggacin cmc-B having the following formula V:

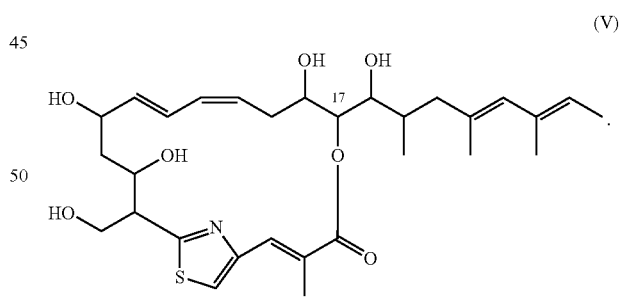

(V)

As described for the migration of the lacton bond formed in thuggacin C with C-18 to the formation of the lacton bond to C-16 in thuggacin A, the lacton bond formed in thuggacin cmc-A (IV) with C-16 formally migrates to C-18 in thuggacin cmc-C. During this reaction, the intermediate structure of thuggacin cmc-B occurs and can be isolated, in which the lacton bond is formed with C-17. Accordingly, thuggacin cmc-B is a structural isomer of thuggacin cmc-A and thuggacin cmc-C with the lacton bond formed with C-17 instead of C-16 and C-18, respectively. This structural variation caused by migration of the lacton bond has been observed for the rearrangement reactions between thuggacin A, thuggacin B and thuggacin C, respectively and supports the assumption of related synthetic pathways during fermentation. Further, the rearrangement reactions of thuggacins A, B and C as well as of thuggacins cmc-A, cmc-B and cmc-C, respectively, follow the same formal mechanism and both result in transesterification rearrangement products between carbon atoms in the same positions and therefore demonstrate the chemical relationship, e.g. the chemical homogeneity, between the thuggacin structures of the present invention.

The antibacterial effect, preferably also against *Mycobacterium tuberculosis*, can also be demonstrated for thuggacin cmc-A, thuggacin cmc-B and thuggacin cmc-C, respectively. Accordingly, the present invention also provides the use of thuggacin cmc-A, thuggacin cmc-B and/or thuggacin cmc-C, respectively, for the production of a composition for medical use, especially for use against mycobacterial infections, e.g. against infections by *Mycobacterium tuberculosis* or *Mycobacterium leprae*. The potency against *Mycobacterium leprae* can at present not be tested in vitro but can reasonably be assumed on the basis of its relationship with *M. tuberculosis*.

DETAILED DESCRIPTION OF THE INVENTION

The present invention will now be described in greater detail by examples with reference to the Figure showing analytical data of the equilibrium reaction of thuggacin A in a protic solvent, namely methanol.

EXAMPLE 1

Isolation of Thuggacin C

For producing thuggacin C, *Sorangium cellulosum* strain So ce895 (obtainable from DSMZ under accession number 10320) was cultivated in a medium of soluble starch, 0.6%; yeast extract, 0.2%; $KNO_3$, 0.04%; $NH_4Cl$, 0.06%; $CaCl_2 \times 2H_2O$, 0.1%; $MgSO_4 \times 7H_2O$, 0.1%; glucose$\times 7H_2O$, 0.35%; Na—Fe-EDTA, 8 mg/L; HEPES, 1%; XAD-16 adsorber resin, 1%. Before autoclaving, the pH was adjusted to 7.4 using KOH. The further conditions were: inoculum, 2% (v/v); temperature, 30° C.; stirring rate, 80/min; aeration, 0.5 L/(L medium×min) until the $pO_2$ was decreased to 20%. Then it was kept at this value by variation of the stirring rate.

For isolation of thuggacins, about 3 L XAD adsorber resin and 1.5 L wet cell mass were harvested by centrifugation from 300 L fermentation broth and contacted with acetone for extraction. After evaporation of the acetone, the remaining aqueous phase was extracted with dichloromethane, resulting in 26.6 g crude material after drying and evaporation. The crude material was partitioned between methanol and heptane, reducing the weight of the more polar material to 15.6 g dry matter. The residue was dissolved in ice-cold ethylacetate extracted three times with cold aqueous sodium carbonate (1%) and then with cold saturated sodium chloride solution to yield 5.3 g of crude thuggacin compounds from the ethylacetate phase.

Flash chromatography on silica gel using a gradient of increasing polarity provided a fraction enriched in thuggacin A and thuggacin B, which could be separated further by reversed phase chromatography.

The thuggacin containing residue was dissolved in DCM and transferred to a column of silica gel (200 mL, 0.063-0.200 mm), which was eluted with DCM (500 mL), DCM/acetone (9:1) (400 mL), DCM/acetone/methanol (90:9:1) (400 mL), DCM/acetone/methanol (90:5:5) (400 mL), and 300 mL of DCM/methanol (9:1). The last fraction provided 1.5 g of raw thuggacins, which were separated by RP-chromatography [column 40×530 mm, Eurosil Bioselect C18 100-20, 15-25µ, solvent A=water, B=methanol, gradient: 65% B for 76 min, from 65% to 80% B in 120 min, 80% B for 100 min, to 100% B in 60 min; flow 17 mL/min; detection UV-absorption at 226 nm to give 244 mg of thuggacin A (1) [$t_R$ about 240 min] and 61 mg of thuggacin B (2) [$t_R$ about 200 min]. Thuggacin A was crystallized from ether/petroleum benzine.

As a derivative of thuggacin A, 13-methyl-thuggacin A could be isolated as a peak fraction eluting immediately following the thuggacin A fraction. The fraction was purified further by RP-HPLC with a gradient of 80% methanol to 90% methanol in 15 min on a column (250×21 mm) of Nucleodur 100-10 C18 (obtainable from Macherey-Nagel). The main peak (UV-detection at 232 nm) of two injections was collected and evaporated to give 16 mg 13-methyl-thuggacin A. Analytical results are $[\alpha]^{22}_D=-127.7$ (c=0.94, in methanol); UV (methanol): λmax (lg ε)=227 (4.622), 286 (4.038); MS: (EI, 200° C.): m/z (%)=645 (9), 627 (34), 609 (18), 591 (19), 384 (9), 320 (16), 304 (26), 267 (60), 250 (100); (−)-DCI-MS ($NH_3$): m/z (%)=645 (100); (+)-DCI-MS ($NH_3$): m/z (%)=646 (100); HR-EI MS: $C_{36}H_{55}NSO_7$ calculated 645.3699, found 645.3649; $C_{36}H_{53}NSO_6$ calculated 627.3593, found 627.3573.

From the correlation of the 13-methyl group with 11-H and 14-H in the $^1$H, $^1$H ROESY NMR spectrum and the correlation of 12-H with 3-H and methylene-15, it was concluded that the 13-methyl-thuggacin A has the same s-trans E,Z double bond configuration as thuggacin A and thuggacin B. The structure of 13-methyl-thuggacin A is given as VII below:

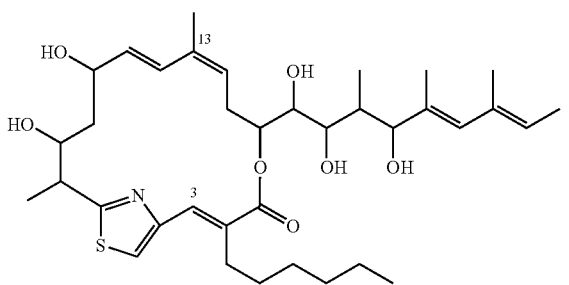

(VII)

Thuggacin C could be isolated from the thuggacin mixture obtained from the fermentation by chromatography or from the transesterification reaction of thuggacin A and/or thuggacin B in aqueous solution in presence of methanol. For chromatography, preparative RP-HPLC (Nucleodur 100-10 C18, Macherey-Nagel, with solvent A=methanol 50%, solvent B=methanol, 40% B (=70% MeOH) for 15 min, gradient to 60% B (80% MeOH) in 45 min, 60% B for 20 min; flow 18 mL/min; detection UV-absorption at 225 nm) was used.

NMR analysis confirmed the structures given for thuggacin A, thuggacin B and thuggacin C.

TABLE 1

NMR data of thuggacin A and thuggacin C in DMSO-$d_6$.[a]

| | Thuggacin A[b] | | | | Thuggacin C[b] | | | |
|---|---|---|---|---|---|---|---|---|
| No. | $δ_H$ | m | J | $δ_C$ m | $δ_H$ | m | J | $δ_C$ m |
| 1 | —.— | — | — | 166.48 s | — | — | — | 166.84 s |
| 2 | —.— | — | — | 131.90 s | — | — | — | 133.65 s |
| 3 | 7.77 | s | — | 132.94 d | 7.69 | s | — | 130.64 d |
| 4 | —.— | — | — | 149.04 s | — | — | — | 149.89 s |
| 5 | 7.72 | s | — | 118.94 d | 7.84 | s | — | 121.64 d |
| 6 | — | — | — | 171.24 s | — | — | — | 172.30 s |
| 7 | 3.38 | dq | 9.2, 6.8 | 43.30 d | 3.38 | dq | 8.0, 6.8 | 43.77 d |
| 8 | 3.52 | dt | 9.4, 3.6 | 75.70 d | 3.58 | ddd | 3.7, 4.8, 8.0 | 74.08 d |
| 8-OH | (5.00 | d | 6.6) | —.— — | (5.12 | d | 6.4) | — — |
| 9a | 1.69 | ddd | 14.9, 9.1, 3.8 | 39.87 t | 1.63 | m | 10.2, 5.3[c] | 39.62 d |
| 9b | 0.61 | dd | 13.6, 3.0, br. | | 1.05 | dt | 14.1, 3.3 | |
| 10 | 4.85 | dd | 9.2, 9.1 | 69.69 d | 4.18 | ddd | 3.4, 7.7, 10.1 | 69.07 d |
| 10-OH | (5.01 | d | 3.1) | —.— — | (5.06 | d | 3.8) | — — |
| 11 | 5.39 | dd | 9.2, 14.9 | 137.33 d | 5.46 | dd | 7.9, 15.1 | 136.76 d |
| 12 | 6.41 | dd | 10.9, 15.1 | 124.76 d | 6.09 | dd | 11.3, 15.1 | 124.92 d |
| 13 | 5.84 | t | 10.9 | 130.89 d | 5.83 | tt | 11.1, 1.6 | 127.65 d |
| 14 | 5.24 | dt | 5.3, 11.3 | 127.85 d | 5.48 | dt | 3.9, 10.0 | 130.98 d |
| 15a | 2.79 | ddd | 11.5, 11.3, 14.1 | 29.89 t | 2.79 | dd | 9.1, 16.4 | 29.53 t |
| 15b | 2.24 | dd | 5.3, 14.3, br. | | 1.53 | ddt | 16.4, 10.8, 2.9 | |
| 16 | 4.86 | ddd | 11.0, 3.5, 1 | 74.24 d | 3.52 | dd | 5.3, 10.9 | 72.14 d |
| 16-OH | — | — | — | — — | (4.93 | d | 4.5) | — — |
| 17 | 3.58 | dd | 3.8, 6.4 | 72.05 d | 3.76 | d | 5.5 (br) | 70.89 d |
| 17-OH | (4.87 | m | —) | —.— — | (5.29 | d | 5.3) | — — |
| 18 | 3.46 | dd | 3.0, 6.4 | 71.44 d | 5.18 | d | 7.2 | 73.47 d |
| 18-OH | (4.30 | d | 5.5) | —.— — | — | — | — | — |
| 19 | 1.85 | ddq | 3.0, 6.4, 6.8 | 37.17 d | 2.20 | ddq | 7.0, 3.4, 7.2 | 36.88 d |
| 20 | 3.87 | d | 6.0 | 77.43 d | 4.05 | d | 2.6 (br) | 73.74 d |
| 20-OH | (4.62 | d | 3.0) | —.— — | (5.00 | d | 4.1) | — — |
| 21 | —.— | — | — | 135.82 s | — | — | — | 135.65 s |
| 22 | 5.78 | s | br. | 128.35 d | 5.89 | s | br. | 127.80 d |
| 23 | —.— | — | — | 133.07 s | — | — | — | 133.03 s |
| 24 | 5.24 | dq | 1.0, 7.2 | 123.01 d | 5.32 | q | 6.7 (br) | 123.07 d |
| 25 | 1.55 | d | 6.8 | 13.42 q | 1.63 | d | 6.7 | 13.50 q |
| 26a | 2.48 | m | [d] | 26.66 t | 3.02 | ddd | 6.6, 8.7, 12.6 | 27.19 t |
| 26b | 2.30 | ddd | 7.1, 7.1, 13.3 | | 2.59 | ddd | 6.4, 8.5, 12.6 | |
| 27 | 1.31 | m | | 27.60 t | 1.43 | m | — | 28.14 t |
| 28a | 1.31 | m | — | 28.37 t | 1.31 | m | — | 28.61 t |
| 28b | 1.21 | m | — | | | | | |
| 29 | 1.17 | m | — | 31.10 t | 1.23 | m | — | 31.08 t |
| 30 | 1.17 | m | — | 21.93 t | 1.23 | m | — | 21.93 t |
| 31 | 0.78 | m | — | 13.85 q | 0.80 | m | — | 13.88 q |
| 32 | 1.44 | d | 6.8 | 17.39 q | 1.42 | d | 6.8 | 17.44 q |
| 33 | 0.77 | m | — | 8.21 q | 0.74 | d | 7.2 | 9.40 q |
| 34 | 1.60 | s | — | 14.18 q | 1.62 | s | — | 15.34 q |
| 35 | 1.64 | s | — | 16.68 q | 1.69 | s | br | 16.75 q |

[a]$^1$H 600 MHz; $^{13}$C 150 MHz.
[b]Data after H/D exchange; selected data of OH-form in brackets.
[c]A part was under methyl C-34 signal;
[d]With solvent signal. Values are real data and include measuring inaccuracies.

For thuggacin C, the following data were determined: $[α]^{22}_D$=−35.7 (c=0.7, in methanol). UV (methanol): $λ_{max}$ (lg ε)=228 (4.555), 286 (4.054). HR-ESI-MS: $C_{35}H_{53}NSO_7$+H$^+$ calculated 632.3615, found 632.3623.

EXAMPLE 2

Production of Thuggacin cmc-A, Thuggacin cmc-B and Thuggacin cmc-C by Fermentation of Chondromyces For the production of thuggacin cmc-A, thuggacin cmc-B and thuggacin cmc-C, *Chondromyces crocatus* (strain Cm c5, accession number DSM 10034) was cultivated under the following conditions: Bioreactors (900 L) used were supplied by Giovanola Fréres, Monthey, Switzerland; periphery modified by applicant, equipped with 2 turbine plate stirrers and a capacity of about 900 L. Medium: Probion (single-cell protein from Methylomonas clarae; Hoechst Frankfurt) 0.4%; soluble starch 0.3%; $MgSO_4.7H_2O$ 0.2%; $CaCl_2·2H_2O$ 0.05%; vitamin $B_{12}$ 0.25 mg/ml; 1 mL/L standard trace element solution (Schlegel, Allgemeine Mikrobiologie); pH 7.0 to 7.1. Optionally, the medium contained 1% Amberlite XAD-16 (Rohm and Haas, Frankfurt) as an adsorber resin. In the bioreactor, 600 L of medium were inoculated with 60 to 90 L of a well grown culture from a seed fermenter. The preferred cultivation temperature is 30° C. The aeration rate is set to 55 to 80 standard L/min and the stirrer speed to 50 rpm. Because the fermentation broth produces a large amount of foam, 0.05% of the anti-foam Tegosipon (obtainable from Goldschmidt Essen) is added. The $pO_2$ value, which is 95 to 90% saturation at the beginning of fermentation, decreased to about 75 or 40% at the end of the fermentation after 91 to 96 hours. The initial pH value decreased from 7.0 slightly into the acid range (pH 6.9), then rose during the fermentation to 7.6 after 74 hours and was then kept at 7.4 to 7.6 by titration with 30% acetic acid until the end of the fermentation The crude acetone extract of cells, optionally including the XAD adsorber resin present during the cultivation, which were harvested from the fermentation broth (total volume 660 L) by centrifugation, was evaporated to give an oily residue (about 180 g), which was subjected to a methanol-heptane partition [800 mL methanol (3% water) and 600 mL heptane in 3 portions] in order to remove lipophilic byproducts. About 65 g material was recovered after evaporation of the methanol layer. Large scale RP-chromatography with a stepwise gradient of 75%, 80%, 85% and 100% MeOH provided fractions, which were combined according to HPLC analysis. The first fraction, eluted with 75% MeOH, contained the polar compounds (e.g. chondramides) and thuggacins followed by a fraction containing chondrochlorens. The first fraction of about 8.6 g was again separated by RP-chromatography with a solvent gradient between 50% and 70% of aqueous methanol containing 0.2% acetic acid. After HPLC analysis, similar fractions were combined and provided three consecutive fractions of about 70 mg (I), 280 mg (II) and 220 mg (III) containing different thuggacin-variants, which were eluted between the more polar chondramides and more lipophilic chondrochlorens. These fractions were separated further by LH-20 chromatography (solvent methanol) to give thuggacin cmc-B (~30 mg) from (I). From the LH-20 fractions of (II) and (III), a further separation by silica gel PSC provided thuggacin cmc-C (38 mg) and cmc-A (70 mg), respectively.

Analytical reverse phase HPLC gave the following results: Column 125×2 mm, Nucleosil C18, pre-column 10×2 mm; solvent A=water, solvent B=methanol, gradient 60% B for 3 min, 60 to 70% B 6 min, 70 to 90% B 3 min, 100% B 3 min, 100 to 60% 0.5 min, 60% 3 min, flow 0.3 mL/min; detection UV absorption at 220-224 nm: Rt=ca. 8.3-9.5 min thuggacin cmc-B; Rt=ca. 9.9-10.9 min thuggacin cmc-C; Rt=ca. 10.5-11.6 min thuggacin cmc-A.

NMR analysis of thuggacin cmc-A and thuggacin cmc-C yielded the following signals:

TABLE 2

NMR data of thuggacins cmc-A and cmc-C in $[D_6]DMSO^{[a]}$.

| | Thuggacin cmc-A | | | | | Thuggacin cmc-C | | | |
|---|---|---|---|---|---|---|---|---|---|
| No. | $\delta_H$ | m | $J^{[b]}$ | $\delta_C$ | m | $\delta_H$ | m | J | $\delta_C$ | m |
| 1 | — | — | — | 166.86 | s | — | — | — | 167.33 | s |
| 2 | — | — | — | 125.99 | s | — | — | — | 127.90 | s |
| 3 | 7.87 | s | — | 133.46 | d | 7.80 | s | (br.) | 131.33 | d |
| 4 | — | — | — | 148.98 | s | — | — | — | 149.63 | s |
| 5 | 7.82 | s | — | 121.01 | d | 7.93 | s | — | 123.14 | d |
| 6 | — | — | — | 167.97 | s | — | — | — | 169.31 | s |
| 7 | 3.44 | m | (3.6, 5.5, 9.5) | 51.37 | d | 3.48 | m | — | 51.54 | d |
| 8 | 3.88 | m | (9.7, 3.5, 3.5) | 70.09 | d | 3.86 | m | — | 69.86 | d |
| 8-OH | 5.00 | d | 6.5 br | — | — | 5.18 | d | 5.0 | — | |
| 9a | 1.64 | m | — | 39.26 | t | 1.60 | ddd | 3.7, 10.5, 14.5 | 39.17 | t |
| 9b | 0.43 | dd | 14.3, 2 br | | | 0.78 | m | — | | |
| 10 | 4.94 | dd | 9.2, 9.5 | 69.55 | d | 4.73 | dd | 8.0, 10.0 (br.) | 69.35 | d |
| 10-OH | 5.05 | d | 2.0 br | — | — | 5.25 | s | (br.) | — | |
| 11 | 5.39 | dd | 15.1, 9.2 | 137.16 | d | 5.48 | dd | 8.0, 15.0 | 136.67 | d |
| 12 | 6.46 | dd | 15.1, 11.1, | 125.03 | d | 6.19 | dd | 11.3, 15 | 124.66 | d |
| 13 | 5.87 | dd | 10.0, 11.0 | 130.95 | d | 5.83 | dd | 10.9, 11.3 | 127.52 | d |
| 14 | 5.30 | ddd | 11.4, 11.4, 5.4 | 128.02 | d | 5.50 | ddd | 3.5, 9.7, 10.9 | 131.08 | d |
| 15a | 2.86 | ddd | 13.7, 11.6, 11.5 | 29.97 | t | 2.87 | dd | 9.7, 16.0 | 29.24 | t |
| 15b | 2.24 | dd | 13.7, 5.1 | | | 1.44 | ddt | 11.5, 16, 3 | | |
| 16 | 4.90 | dd | 10.8, 3.3 br | 74.25 | d | 3.46 | m | — | 72.45 | d |
| 16-OH | — | — | — | — | — | 4.96 | m | — | — | — |
| 17 | 3.57 | dd | 6.8, 3.5 (m, br) | 72.10 | d | 3.71 | t | 5.4 | 71.43 | d |
| 17-OH | 4.82 | d | 6.0 br | — | — | 5.04 | d | 6.0 | — | — |
| 18 | 3.33 | dd | 6.8, 3 (m, br) | 71.84 | d | 4.96 | m | — | 74.81 | d |
| 18-OH | 4.31 | d | 6.0 br | — | — | — | — | — | — | — |
| 19 | 1.94 | m | — | 32.33 | d | 2.20 | dddq | 4.0, 6.8, 10.3, 6.8 | 32.51 | d |
| 20a | 2.12 | dd | 12.9, 6.5 | 45.21 | t | 2.32 | dd | 4.0, 13.2 | 44.40 | t |
| 20b | 1.77 | dd | 12.9, 7.8 | | | 1.80 | dd | 10.3, 13.2 | | |
| 21 | — | — | — | 133.27 | s | — | — | — | 132.96 | s |
| 22 | 5.59 | s | — | 130.19 | d | 5.63 | s | (br.) | 130.37 | d |
| 23 | — | — | — | 133.27 | s | — | — | — | 133.15 | s |
| 24 | 5.22 | q | 7.0, br | 122.64 | d | 5.30 | q | 6.8 (br.) | 122.87 | d |
| 25 | 1.59 | d | 7.0 | 13.46 | q | 1.63 | d | 6.8 | 13.44 | q |
| 26 | 1.95 | s | br | 13.35 | q | 2.26 | s | — | 14.54 | q |
| 32 | 3.94 | m | | 59.80 | t | 3.98 | ddd | 4.0, 5.0, 10.4 (br.) | 60.55 | t |
| | | | | | | 3.89 | m | — | | |
| 32-OH | 5.17 | t | 4.3 br | — | — | 5.12 | t | 4.0 | — | |
| 33 | 0.76 | d | 6.5 | 13.64 | q | 0.79 | d | 6.8 | 15.28 | q |
| 34 | 1.70 | s | br | 17.67 | q | 1.69 | s | — | 17.41 | q |
| 35 | 1.63 | s | — | 16.68 | q | 1.68 | s | — | 16.68 | q |

[a]$^1$H: 600 MHz, $^{13}$C: 150 MHz.
[b]Values in brackets after H/D exchange.

In further analyses, the following data were obtained: Thuggacin cmc-A: $[\alpha]^{22}_D=-160.6$ (c=1.24, in methanol). UV (methanol): $\lambda$max (lg $\epsilon$)=224 (4.672), 285 (4.085). MS: (EI, 200° C.): m/z (%)=561 (37), 543 (66), 525 (22), 452 (24), 382 (23), 294 (27), 196 (62), 178 (100). (−)-DCI-MS (NH$_3$): m/z (%)=561 (100); HR-EI MS: $C_{30}H_{43}NSO_7$ calculated 561.2760; found 561.2894; $C_{30}H_{41}NSO_6$ calcd. 543.2654, found 543.2649.

For thuggacin cmc-B, the following analytical results were found: Molecular Formula =$C_{30}H_{43}NO_7S$, formula weight=561.73. Selected $^1$H NMR signals [400 MHz, methanol-d$_4$ ($\delta$=3.31 ppm)] $\delta$ [ppm]=0.95 (d, J=6.9 Hz, 3H), 1.66 (d, J=6.9 Hz, 3H), 1.70 (s, 3H), 1.76 (s, 3H), 1.84-1.93 (ddd, J=14.5, 8.4, 5.3 Hz, 1H), 2.24 (d, J=1 Hz, 3H), 2.68 (dt, J=14.4, 11 Hz, 1H), 3.46 (m, 1H), 3.54-3.61 (m, 1H), 3.90 (dt br., J=11, 2 Hz, 1H) 3.94-4.08 (m, 3H), 4.15 (m, 1H), 5.05 (dd, J=7.5, 1.6 Hz, 1H), 5.32 (q br., J=6.6 Hz, 1H), 5.48 (td, J=10.6, 4.5 Hz, 1H), 5.64 (dd, J=15.3, 6.1 Hz, 1H), 5.69 (s br., 1H), 6.08 (t, J=10.8 Hz, 1H), 6.26 (dd, J=15.2, 11.1 Hz, 1H), 7.78 (s, 1H), 8.29 (s, 1H). (+) DCI MS (NH$_3$) m/z (%)=562 (100), 544 (−24). (−) DCI MS (NH$_3$) m/z (%)=561 (100).

Thuggacin cmc-C: $[\alpha]^{22}_D=-47.4$ (c=0.5, in methanol). UV (methanol): $\lambda_{max}$ (lg $\epsilon$)=227 (4.640), 285 (4.135). MS: (EI, 200° C.): m/z (%)=561 (28), 543 (63), 525 (14), 452 (24), 382 (26), 294 (27) 178 (100); (−)-DCI-MS (i-butane): m/z (%)=561 (100); (+)-DCI-MS (i-butane): m/z (%)=562 (100), 544 (74); HR-EI MS: $C_{30}H_{43}NSO_7$ calcd. 561.2760; found 561.2802; $C_{30}H_{41}NSO_6$ calculated 543.2654, found 543.2646.

The $^1$H NMR signals of H-3 and H-5 are characteristic of thuggacin variants with different lactone ring sizes. For example, the corresponding singlett signals of thuggacin cmc-B at 8.29 and 7.78 ppm in methanol-d$_4$ are comparable to the measurements for thuggacin B (8.23 and 7.65 ppm). Further, the lactone 17-H signal at 5.05 ppm (dd, J=7.5, 1.6 Hz, 1H) of thuggacin cmc-B is comparable with the corresponding signal at 5.07 (dd, J=7.7, 1.7 Hz, 1H) of thuggacin B. These similarities support the structural relationships between the compounds of the invention.

EXAMPLE 3

Stabilisation of an Aqueous Composition Comprising Thuggacin A, Thuggacin B, Thuggacin C When analyzing an aqueous composition, optionally including methanol, comprising one of thuggacin A, thuggacin B and thuggacin C, it was found that transesterification products could be identified, indicating the rearrangement of thuggacins in respect of the formation of the lacton bond. Starting from 8 mg/mL thuggacin A, an equilibrium of thuggacin A, thuggacin-B and thuggacin C could be found after approximately 96 hours. Analytical results are shown in FIG. 1. In general, the reaction time for reaching the equilibrium can vary over a broad range, e.g. from 1 to 20 days. Re-crystallized thuggacin of high purity is nearly stable, i.e. undergo rearrangement only very slowly. Thuggacin A having a lower purity will undergo rearrangement to thuggacin B and C with increased reaction rates. Similar stabilities have been observed for the rearrangement reaction of thuggacin cmc-A to thuggacin cmc-B and cmc-C.

For stabilisation, any proportion of thuggacin A, thuggacin B and thuggacin C, independent from the equilibrium concentrations could be maintained by adding to the aqueous solution, optionally comprising an alcohol, of an acid, preferably of an organic acid, e.g. acetic acid. Preferred concentrations of the acid are in the range of 1 to 500, preferably 1 to 100, more preferably 5 to 50 mmoles/L, with a pH preferably in the range of 4.5 to 7.

As the thuggacins of the invention show the rearrangement of the lacton bond, it is preferred for the compounds and compositions of the invention that they contain an acid, preferably an organic acid for stabilisation of the concentration of each of thuggacin A, B, C, cmc-A, cmc-B and cmc-C.

EXAMPLE 4

Antibiotic Activity of Thuggacins Against *Mycobacterium tuberculosis*

Initial studies using *Micrococcus luteus* showed that thuggacin A was acting to inhibit oxygen consumption almost completely, which correlates with the finding that the oxidation of NADH and of reduced cytochrome c were reduced. Presently, it is assumed that thuggacins inhibit the activity of the later steps of the respiratory chain of sensitive bacteria.

Initial experiments in liquid culture showed MIC of between 0.03 to 0.6 µg/mL for *Micrococcus luteus, Mycobacterium phlei* and *M. chitae* when tested against single thuggacins. In these experiments, thuggacin A and thuggacin B as well as thuggacin cmc-A and thuggacin cmc-B were most effective. Interestingly, thuggacin C was less effective against certain bacteria. In contrast to the effect on gram-positive bacteria, cultivated animal cells were affected to a much lower extent, e.g. cultivated mouse fibroblast cells (L929) were only moderately sensitive to thuggacins (IC$_{50}$=4 µg/mL for thuggacin A, IC$_{50}$=8 µg/mL for thuggacin B).

Using the standard *Mycobacterium tuberculosis* test strain H375RV, it could be shown that thuggacin A inhibited growth at or below 8 µg/mL in liquid culture.

In an agar diffusion test using 10 µg of the compound per disc, the following inhibition was found:

| | Diameter of inhibition zone (mm)* | | |
|---|---|---|---|
| | thuggacin | | |
| Test organism | thuggacin A | cmc-A | thuggacin cmc-C |
| *Micrococcus luteus* | 29 | 46 | 44 |
| *Corynebacterium fascians* | (30) | (47) | (44) |
| *Mycobacterium phlei* | 20 | 24 | 22 |

*Figures in parentheses indicate an incomplete inhibition. Stock solutions of thuggacins contained DMSO.

For tests of the biological activity, preferably aqueous compositions of the thuggacins according to the present invention were used separately in an aqueous composition comprising 10 mM acetic acid for stabilisation.

Similar to the activity of thuggacin A, biological activity for thuggacin B, thuggacin C, 13-methyl thuggacin A, thuggacin cmc-C, thuggacin cmc-B and thuggacin cmc-A were determined, preferably against the standard test strain and, more preferably, against clinical isolates of *Mycobacterium tuberculosis*.

The invention claimed is:

1. A pharmaceutical composition comprising, as an effective ingredient, at least one compound effective against pathogenic mycobacteria, the compound comprising a structure selected from the group consisting of thuggacin C (III)

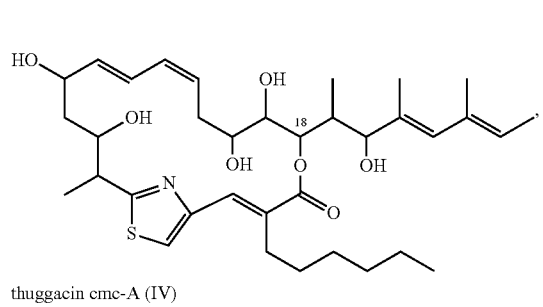

thuggacin cmc-A (IV)

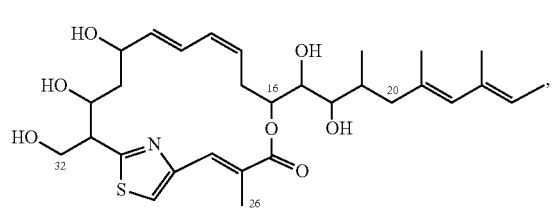

thuggacin cmc-B (V)

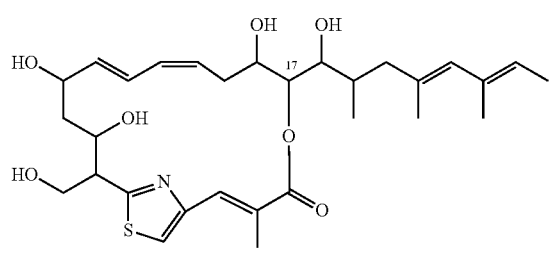

and thuggacin cmc-C (VI)

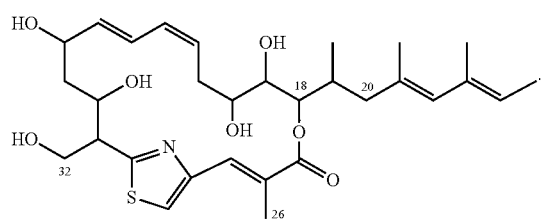

2. A pharmaceutical composition comprising 13-methyl thuggacin A as an effective ingredient against pathogenic mycobacteria.

3. The composition of claim 1 wherein the composition comprises at least one acid, base or buffer substance to provide for a pH in the range from 3.5 to 9.

4. The composition of claim 1, wherein the acid, base or buffer is selected from the group comprising pharmaceutically acceptable substances.

5. A compound having the structure of thuggacin C (III)

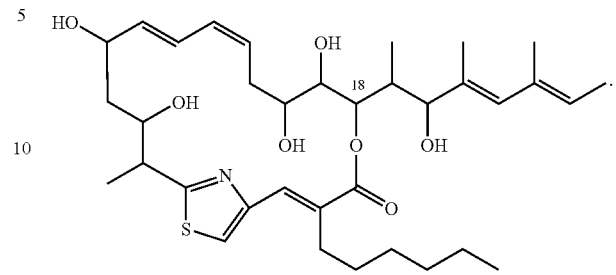

6. A compound having the structure of thuggacin cmc-A (IV)

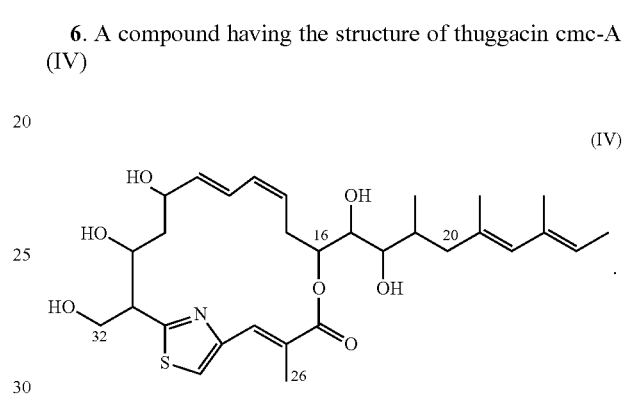

7. A compound having the structure of thuggacin cmc-B (V)

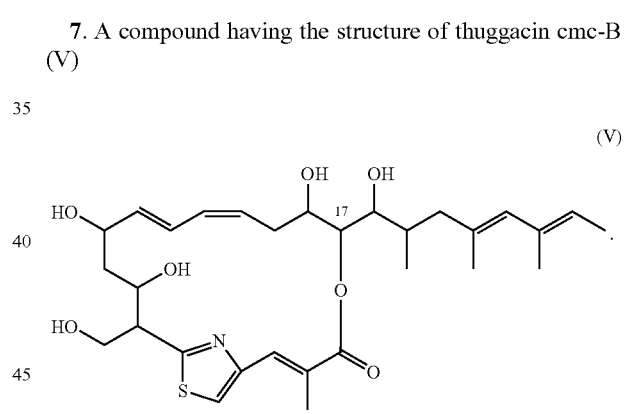

8. A compound having the structure of thuggacin cmc-C (VI)

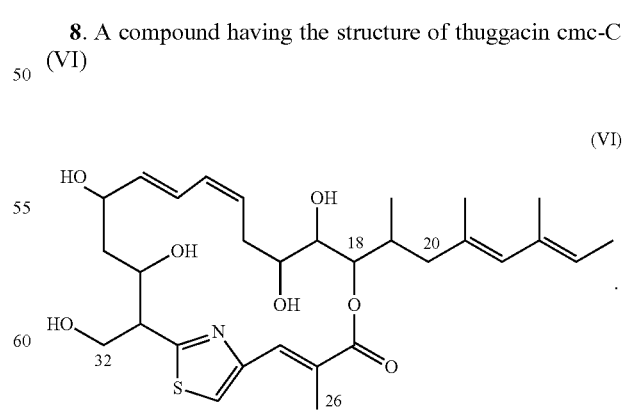

9. A pharmaceutical composition comprising the compound according to claim 5, wherein the pharmaceutical composition is effective against pathogenic mycobacteria.

10. A pharmaceutical composition comprising the compound according to claim 6, wherein the pharmaceutical composition is effective against pathogenic mycobacteria.

11. A pharmaceutical composition comprising the compound according to claim 7, wherein the pharmaceutical composition is effective against pathogenic mycobacteria.

12. A pharmaceutical composition comprising the compound according to claim 8, wherein the pharmaceutical composition is effective against pathogenic mycobacteria.

13. The composition of claim 3, wherein the composition is in a protic solvent.

14. The composition of claim 13, wherein the protic solvent is selected from the group consisting of alcohol, acetone and DMSO.

* * * * *